United States Patent
MacCarter et al.

(10) Patent No.: US 6,858,006 B2
(45) Date of Patent: Feb. 22, 2005

(54) CARDIOPULMONARY MONITORING

(75) Inventors: Dean J. MacCarter, Englewood, CO (US); Andreas N. Hadjicostis, Lone Tree, CO (US); John K. Buckner, Littleton, CO (US)

(73) Assignee: Wireless Medical, Inc., Englewood, CO (US)

(*) Notice: Subject to any disclaimer, the term of this patent is extended or adjusted under 35 U.S.C. 154(b) by 0 days.

(21) Appl. No.: 09/948,997

(22) Filed: Sep. 7, 2001

(65) Prior Publication Data

US 2002/0082867 A1 Jun. 27, 2002

Related U.S. Application Data

(60) Provisional application No. 60/231,410, filed on Sep. 8, 2000.

(51) Int. Cl.⁷ ................................................. A61B 5/00
(52) U.S. Cl. .................. 600/300; 600/301; 600/538; 128/903; 128/904; 128/920
(58) Field of Search .............................. 600/300–301, 600/534–538, 549, 481–486, 508–509, 529, 531–532, 587; 128/920–925, 903, 904; 435/7.92; 705/2–4, 11; 702/19

(56) References Cited

U.S. PATENT DOCUMENTS

| | | | |
|---|---|---|---|
| 4,270,547 A | 6/1981 | Steffen et al. | |
| 4,327,741 A | 5/1982 | Watson et al. | |
| 4,452,252 A | 6/1984 | Sackner | |
| 4,622,979 A | 11/1986 | Katchis et al. | |
| 4,815,473 A | 3/1989 | Watson et al. | |
| 5,012,411 A | 4/1991 | Policastro et al. | |
| 5,159,935 A | 11/1992 | Sackner et al. | |
| 5,307,263 A | 4/1994 | Brown | |
| 5,331,968 A | 7/1994 | Williams et al. | |
| 5,613,495 A | 3/1997 | Mills et al. | |
| 5,626,144 A | 5/1997 | Tacklind et al. | |
| 5,732,709 A | 3/1998 | Tacklind et al. | |
| 5,855,550 A | 1/1999 | Lai et al. | |
| 5,862,803 A | 1/1999 | Besson et al. | |
| 5,913,310 A | 6/1999 | Brown | |
| 5,931,791 A | 8/1999 | Saltzstein et al. | |
| 5,941,829 A | 8/1999 | Saltzstein et al. | |
| 5,997,476 A | 12/1999 | Brown | |
| 6,015,388 A | 1/2000 | Sackner et al. | |
| 6,047,203 A | 4/2000 | Sackner et al. | |
| 6,080,106 A | 6/2000 | Lloyd et al. | |
| 6,406,426 B1 * | 6/2002 | Reuss et al. ................. 600/300 |
| 6,425,861 B1 * | 7/2002 | Haberland et al. ........... 600/300 |
| 6,450,955 B1 * | 9/2002 | Brown et al. ................ 600/300 |
| 6,454,707 B1 * | 9/2002 | Casscells, III et al. ...... 600/300 |
| 6,461,828 B1 * | 10/2002 | Stanton et al. ............. 435/7.92 |
| 6,551,252 B2 * | 4/2003 | Sackner et al. ............. 600/536 |

OTHER PUBLICATIONS

LifeChart.com, News Archive, *MedicaLogic/Medscape Strategic Partnership With LifeChart.com to Combine Internet with Wireless Disease Management Programs with Online Consumer Health Records and Clinical Content*, 3 pp, Internet, Jun. 22, 2000, Hillsboro, Oregon and Mountain View, California.

(List continued on next page.)

*Primary Examiner*—Max F. Hindenburg
*Assistant Examiner*—Michael Astorino
(74) *Attorney, Agent, or Firm*—Townsend and Townsend and Crew LLP

(57) ABSTRACT

According to the invention, a system for monitoring health information of a plurality of patients is disclosed. Included in the system are a data gathering device, a node, a wide area network, and a monitoring center. The data gathering device includes a respiration sensor, a wireless transmitter, and a self-contained power source. The node is wirelessly coupled to the data gathering device and the wide area network is coupled to the node. Located remote to the node, the monitoring center is coupled to the wide area network.

18 Claims, 15 Drawing Sheets

OTHER PUBLICATIONS

LifeChart.com, *Clinical Monitoring Services, AirWatch®II*, 1 page, Internet, Nov. 2, 2000.

LifeChart.com, *Managing Cardiovascular*, 1 page, Internet, Nov. 2, 2000.

Piotr Ponikowski, MD, Tuan Peng Chua, MD, Massimo Piepoli, MD, PhD, Waldemar Banasiak, MD, Stefan D. Anker, MD, Roman Szelemej, MD, Wlodzimierz Molenda, MD, Krzysztof Wrabec MD, Alessandro Capucci, MD, and Andrew J.S. Coats, MD, *Ventilatory Response to Exercise Correlates With Impaired Heart Rate Variability in Patients With Chronic Congestive Heart Failure*, The American Journal of Cardiology, vol. 82, Aug. 1, 1998, pp. 338–344.

Yukiko Goso, MD, Hidetsugu Asanoi, MD, Hisanari Ishise, MD, Tomoki Kameyama, MD, Tadakazu Hirai, MD, Takashi Nozawa, MD, Shutaro Takashima, MD; Katsumi Umeno, BS; Hiroshi Inoue, MD, *Respiratory Modulation of Muscle Sympathetic Nerve Activity in Patients with Chronic Heart Failure*, Circulation, Jul. 24, 2001, pp. 418–423.

Applied Digital Solutions (ADS), *What is a Digital Angel?*, Welcome to ADS Digital Angel, Internet, Oct. 19, 2000, pp. 1–10.

INSTROMEDIX (India) PVT. Ltd., *Patient Monitors Model M–011 and Model M–211*, Internet, 1 page, Nov. 2, 2000.

Health Hero Network, *Eckard Corporation Partners with Health Hero Network, Inc. to Deploy Revolutionary Internet–Based Care Program*, Health Hero Network, Inc., Internet, 1 page, Jan. 19, 2000.

BROADCOM, *BCM2033 Single–Chip Bluetooth™System*, BCM2033 Product Brief; Broadcom Corporation, Irvine, California, pp. 1–2.

HomMed, *Making a Difference in Chronic Disease Care*, Internet, pp. 1–9, Apr. 12, 2000.

PULSEMETRIC, Inc., *DynaPulse—Your Non–Invasive Heart Care Link*, sales brochure for DynaPulse 50000A, pp. 1–8, San Diego, California.

Mark Robbins, M.D.; Gary Francis, MD; Fredric J. Pashkow, MD; Claire E. Snader, MA; Kathy Hoercher, RN; James B. Young, MD; Michael S. Lauer, MD, *Ventilatory and Heart Rate Responses to Exercise Better Predictors of Heart Failure Mortality Than Peak Oxygen Consumption*, Circulation, Dec. 14, 1999, Cleveland Clinic Foundation, Cleveland, Ohio, www.circulationaha.org.

\* cited by examiner

CARDIOPULMONARY MONITORING

This application claims the benefit of U.S. Provisional Patent No. 60/231,410 filed on Sep. 8, 2000 which is incorporated by reference herein in its entirety.

BACKGROUND OF THE INVENTION

This invention relates in general to medical monitoring and, more specifically, to cardiopulmonary monitoring.

Congestive heart failure (CHF) is a condition in which the heart is unable to pump enough blood to meet the requirements of the metabolizing tissues in the body, or can do so only at high and ultimately deleterious pressures. Main symptoms are dyspnea (shortness of breath), debilitating fatigue and exertional intolerance. At the advanced stages of CHF the patient is unable to carry out any physical activity without discomfort. Symptoms of heart failure are present even at rest, with increased discomfort upon any level of physical activity. The condition at this stage is inexorably progressive, leading to severe disability and, in the majority of cases, to death.

CHF is currently treated, through the use of drugs, interventional procedures and patient monitoring. Often, a cocktail of drugs is used to lower blood pressure, increase pump efficiency, reduce fluid buildup, limit heart rate, and to thin blood. Interventional procedures include transplants, heart assist devices, valve replacement, angioplasties, stents, and bypass surgery. Patient monitoring may include visits to the doctor's office (averaging 2 to 3 per month), hospital admissions (usually 3 to 4 per year), frequent phone calls to the patient's home by office staff, nurse home visits, home weight checks and home EKG's. Fundamental shortcomings of the current treatment approach are: great demands on physician time, inefficient "fine tuning" of the drug regiment, insufficient patient data collection which are spread far apart and associated high costs.

A tool for evaluating the effect that the above treatment protocols have on a CHF patient is an apparatus called the "metabolic cart." The metabolic cart measures "peak oxygen ($O_2$) consumption" and $CO_2$ output. This method, also known as spirometry, measures $O_2$ consumption, either during resting states or during dynamic exercise (exercise spirometry), to evaluate and quantify by volume calibration, various basic lung volume and expired gas changes under stress effort conditions. These measurements include minute ventilation, tidal volume, inspiratory/expiratory capacity, functional vital capacity, inspiratory reserve, expiratory reserve, respiratory rate, and maximum voluntary ventilation. In addition, mercury-in-silastic strain gauge plethysmography has been used both experimentally and clinically to evaluate breathing patterns in patients with lung disease, sleep apnea, or congestive heart failure, who may present with respiratory trends of periodic breathing or Cheyne-Stokes patterns.

Results from the measurements help evaluate patient status, adjust treatment protocols and improve quality of life. The measurements are also used as a tool for monitoring heart failure deterioration and mortality. In particular, peak $O_2$ consumption is the cornerstone of the cardiac evaluation to determine who is in need of heart transplantation. However, despite their power and usefulness in managing CHF patients, peak $O_2$ consumption measurements are expensive, difficult to carry out and remain largely the domain of research laboratories and CHF specialty clinics.

Even with recent advances in CHF management and improved survival in coronary artery disease and hypertension, CHF mortality has increased fourfold over the last 25 years. Given its increasing prevalence and profound cost in treatment, CHF is a major public health problem. Heart Failure is the leading cause of hospital admission in the USA, accounting for 600,000 admissions per year. There are twice as many admissions for heart failure alone than for all other cardiovascular disease combined. This number continues to increase. Contributing to the increasing cost of CHF is the management aspect, which is physician and time intensive.

BRIEF DESCRIPTION OF THE DRAWINGS

The present invention is described in conjunction with the appended figures.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION OF THE SPECIFIC EMBODIMENTS

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

The present invention provides systems and methods for monitoring health information for patients with heart and/or lung conditions. Small data gathering devices can be positioned on the patient's body to monitor the health of the patient. The medical data gathered is wirelessly relayed to an aggregation node that relays the data to a monitoring center. Medical professionals in contact with the monitoring center can provide health care to the patients from a remote location.

Figure 1:
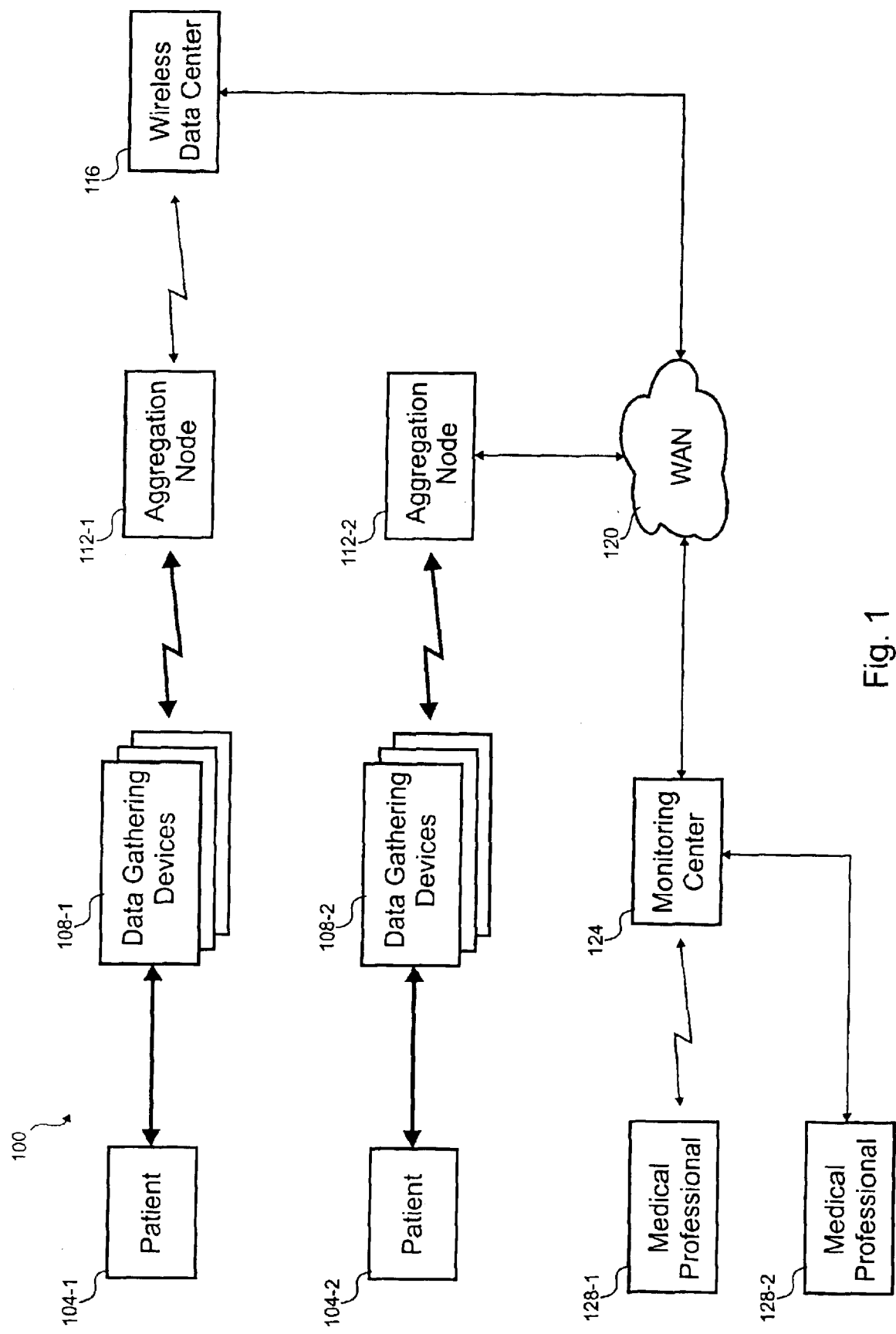
FIG. 1 is a block diagram of an embodiment of a cardiopulmonary monitoring system.

Referring initially to FIG. 1, a block diagram of an embodiment of a cardiopulmonary monitoring system 100 is shown. This embodiment receives monitoring information from any number of patients 104 even though only two are shown in FIG. 1. Each patient 104 has a number of data gathering devices 108 that gather medical data and wirelessly relay that information to an aggregation node 112. With wired or wireless communication, the aggregation node 112 relays the medical data back to a monitoring center 124. Any number of medical professionals 128 can interact with monitoring system 124 to analyze the medical information even though only two medical professionals 128 are shown in the figure.

In this embodiment, the patient 104 is remotely located from a medical professional 128 supervising care. The patient may be suspected of or diagnosed with having any type of cardiopulmonary disease, such as sleep apnea, congestive heart failure, sudden infant death syndrome, arrhythmia, ischemia, lung disease, and/or heart disease. Typically without medical supervision, the patient 104 attaches one or more data gathering devices 108 at the proscribed location on the body. Biocompatible adhesives or clothing harnesses are used to hold the data gathering device 108 in place. Examples of what the data gathering devices 108 could measure include chest wall movement (representative of ventilatory rate or tidal volume), exhaled $CO_2$, heart rate, pulse pressure, blood pressure, oxymetry ($O_2$ saturation), electrocardiogram, peripheral tissue edema, etc.

Each data gathering device 108 has one or more sensors that produce one or more signals that are digitized and wirelessly relayed to the aggregation node 112. In some embodiments, the data gathering device 108 may process the digitized signals prior to wirelessly relaying them to the aggregation node 112. For example, a respiration data gathering device 108 may actually measure chest wall movement. By loading some known, measured parameters of the patient in the data gathering device 108, it can calculate the tidal volume (VT) from the chest wall movement. The VT alone could reported to the aggregation node 112 without all the raw data used to calculate (via a calibration) the VT. Each data gathering device 108 is highly integrated and compact, for example, the two-dimensional skin area of the patient 104 covered could be less than two or four inches.

In some embodiments, a data gathering device 108 has two portions. A first portion is subcutaneous and is in communication with a second portion outside the body that digitizes, processes and wirelessly communicates with the aggregation node 112. The power for the first portion can be self contained or wirelessly provided by the second portion. Although the data gathering devices 108 for this embodiment wirelessly communicate with the aggregation node 112, some embodiments could also include data gathering devices that have wired communication with the aggregation node 112.

The aggregation node 112 is either worn on the body or near the body of the patient 104. The data gathering device transmitter has a limited range. Some embodiments could use Bluetooth™ and have a range of about thirty feet. Other embodiments could use technologies such as 802.11$b$ that has a range of about 300 feet or more. The aggregation node 112 is, at least occasionally, in wireless range of the data gathering devices 108.

A memory on the data gathering devices 108 temporarily store medical data while out of wireless range from the aggregation node. When within range again, the memory sends whatever information is stored and begins to send real-time medical data. When out of range, the frequency of measurement may decrease. In some embodiments, new medical data may simply overwrite the oldest medical data in the memory such only the most recent medical data is stored.

The aggregation node 112 wirelessly communicates with all the data gathering devices 108 associated with the patient 104. The wireless communication includes configuration information and medical data. Configuration information may be sent to the data gathering device 108 by the aggregation node 112, for example, to modify the transmission rate of medical data or provide values used to calculate the medical data. Information sent between the data gathering devices 108 and the aggregation node 112 is secured with encryption, for example. Security allows other aggregation nodes 112 or eavesdroppers from receiving the medical information to protect a patient's privacy and to thwart hackers. Communication from the aggregation node 112 to the monitoring center 124 is also secured for the same reasons.

The aggregation node 112 is a computer that can display medical data, run software, further process the medical data, and communicate with the monitoring center 124. The user interface of the aggregation node 112 is geared for the patient 104 who may have little medical knowledge. Instructions for installation and debugging of problems on the aggregation node are included to reduce customer support demand. The aggregation node 112 can use medical data from a number of data gathering devices 108 to calculate new medical data. For example, respiration medical data could be combined with heart rate and blood pressure medical data to produce an index indicative of the real-time CHF status of the patient 104.

Other information can be entered into the aggregation node 112 such as weight, height, dietary information, sleep times, medication information, etc. to further supplement the medical data received from the data gathering devices 108. Questionnaires can be formulated by the medical professional 128 and supplied to the aggregation node by way of the monitoring center 124 to further aid in diagnosis.

One of the aggregation nodes 112-1 in this embodiment is carried next to the body and wirelessly communicates to the monitoring center 124 by way of a wireless data center 116. A personal digital assistant (PDA), a wireless phone, or other device could be used as the aggregation node 112-1.

The wireless data center 116 provides the wireless service and connects to a wide area network (WAN) 120 that is coupled to the monitoring center 124. The service could be, for example, through a cellular data modem, a wireless Internet connection, a two-way pager network, etc.

The other aggregation nodes 112-2 could have a wired connection to the monitoring center 124 by way of the WAN 120. For example, the aggregation node 112-2 could be a personal computer with an Internet or WAN connection 120 to the monitoring center 124. The connection 120 could use a telephone line, a coaxial cable, a satellite link, optical fiber, a wireless link, etc. Virtual private network (VPN) software could be used to secure the connection over the WAN 120 to the monitoring center 124.

The WAN 120 could be any network that connects computers. In this embodiment, the WAN 120 is the Internet. In other embodiments, the WAN could be a dial-up connection, a leased line, a cellular data connection, a peer-to-peer connection, a point-to-point wireless connection, an ethernet network, etc. If the WAN 120 is insecure, VPN software or other security software may be used to secure the medical data while it passes through the WAN.

The monitoring center 124 is remote to the patients 104 and medical professionals 128 in this embodiment. The monitoring center 124 stores medical data received from the aggregation nodes 112. Configuration information, software and questionnaires are distributed by the monitoring center 124 to the aggregation nodes 112. Pre-designed and custom charts can be viewed by the medical professionals 128 who log into the center 124.

The monitoring center 124 may be staffed or automated. Monitoring software in the center 124 could review the medical data for satisfaction of threshold events entered by the medical professional 128. A staff person or an automated process could notify the medical professional 128 when the threshold event is satisfied. The communication with the medical professional 128 could be wired or wireless.

The monitoring center 124 has a web interface in this embodiment. The medical professional 128 can log into the web interface to view medical data for patients 104 assigned to that medical professional 128. The medical professional 128 could be a doctor or other technician monitoring the care of the patient 104.

Figure 2:
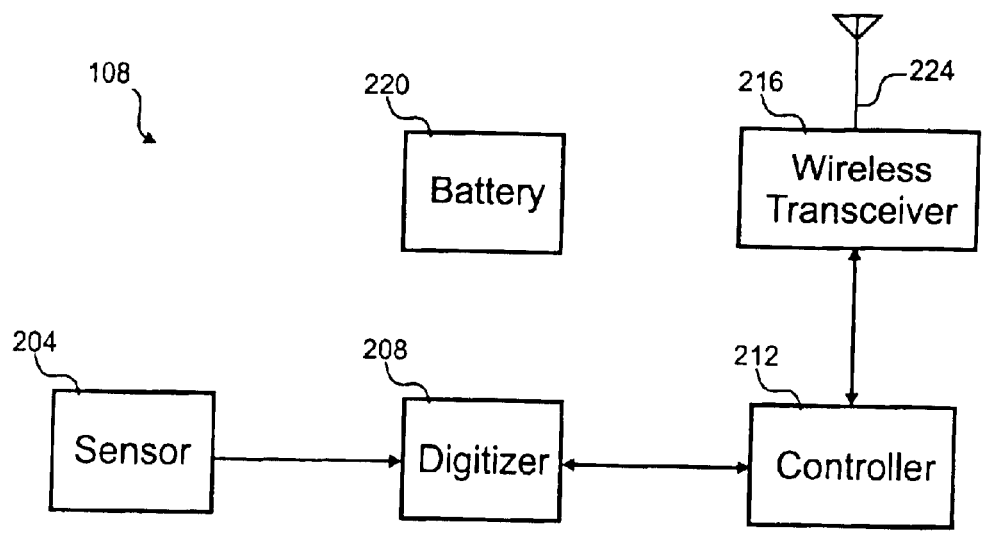
FIG. 2 is a block diagram of an embodiment of a data gathering device.

With reference to FIG. 2, a block diagram of an embodiment of a data gathering device 108 is shown. The data gathering device 108 gathers medical data, processes the data and relays the data to an aggregation node 112. This embodiment includes a battery 220, a sensor 204, a digitizer 208, a controller 212, and a wireless transceiver 216. The battery 220 provides power to the sensor components that require power. Coin-shaped batteries or other compact batteries could be used.

The sensor 204 monitors the patient to provide one or more output signals indicative of the monitoring. Some sensors 204 may have input signals for operating the sensor. The sensor includes an associated circuit that could have both analog and digital circuits to operate the sensor and produce the output signals. The output signals from the sensor 204 are converted to digital form by a digitizer 208 or analog to digital converter.

Once in digital form, the controller 212 may process the digital signal. In this embodiment, the controller includes a digital signal processor to allow refining of the output signals from the sensor 204. The controller 212 also manages communication with the aggregation node 112 using the wireless transceiver 216. A memory in the controller 212 can store the refined output signals if the aggregation node 112 is out of range.

The wireless transceiver 216 communicates using standard protocols in this embodiment. An antenna 224 can be integral to the silicon chip that implements the wireless transceiver 214. Other embodiments can have a compact antenna external to the silicon chip. The wireless transceiver 216 could use Bluetooth™, 802.11b or two-way paging technology. In some embodiments, the wireless transceiver 214 could have longer range to allow communication with the monitoring center 124 in a way that avoided the aggregation node 112 such as two-way paging.

Figure 3A:
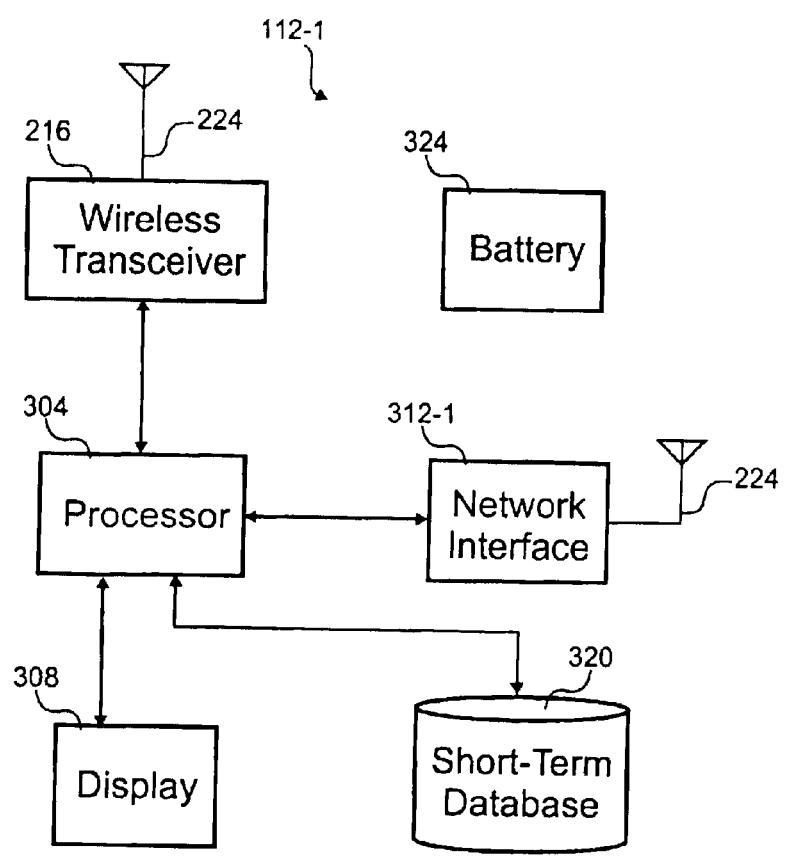
FIG. 3A is a block diagram of an embodiment of an aggregation node that is portable and worn on a patient.

Referring next to FIG. 3A, a block diagram of an embodiment of an aggregation node 112-1 is shown that is portable and worn on the patient 104. For example, a PDA could be used for the aggregation node 112-1 that has Bluetooth™ capability and a cellular modem. This embodiment includes a battery 324, a wireless transceiver 216, a processor 304, a display 308, a short-term database 320, and a network interface 312-1. The battery 324 allows this embodiment to avoid the need for power from a wall socket.

The processor 304 manages the operation of the aggregation node 112-1. Medical data is processed and stored in the short-term database. The processor 314 may send medical data to the monitoring center 124 in real-time or may burst the medical data with occasional connections. The network interface 312-1 wirelessly communicates with a wireless data center 116 remote to the aggregation node 112-1. The patient 104 can interact with a display 308 on the aggregation node that has a touch screen for pen input. Other embodiments could have other input devices, such as mice, keyboards and/or voice recognition.

Figure 3B:
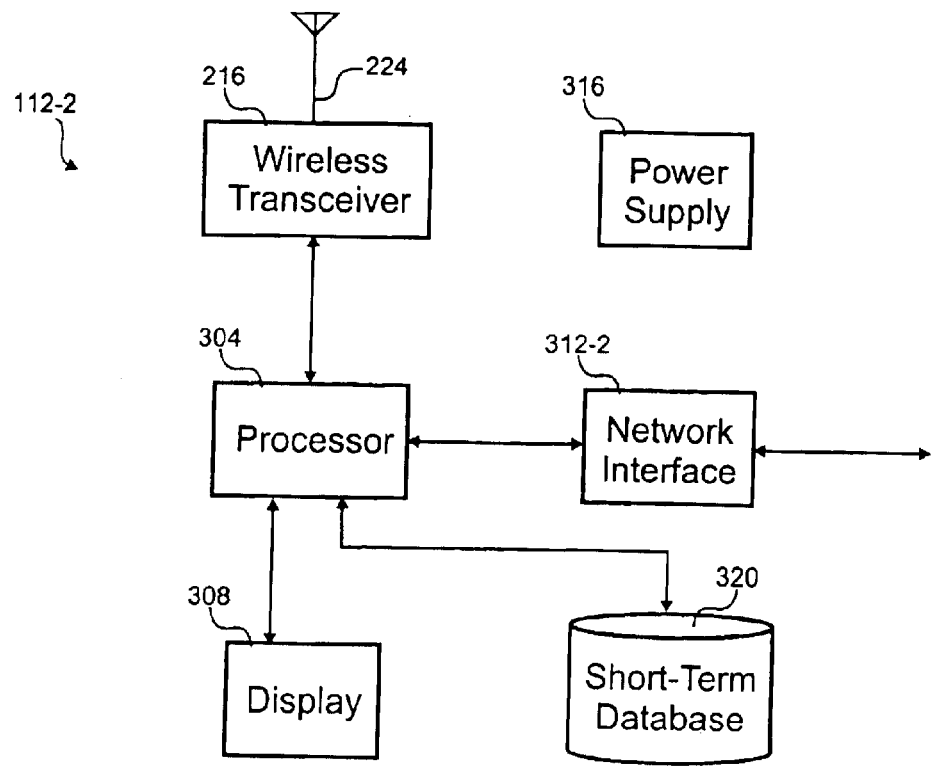
FIG. 3B is a block diagram of another embodiment of the aggregation node that is plugged into a wall outlet.

With reference to FIG. 3B, a block diagram of another embodiment of the aggregation node 112-2 is shown that is plugged into a wall outlet, for example. For example, this embodiment could be a personal computer with a 802.11b wireless ethernet connection and a broadband modem. A power supply 316 is hardwired to a wall outlet to energize the aggregation node 112-2. A network interface 312-2 is wired to the WAN 120 to allow communication with the monitoring center 124. The network interface could be a telephone modem, a satellite modem, a DSL modem, a carrier current modem, a wireless modem, an ethernet network card, or other computer network device.

Figure 4:
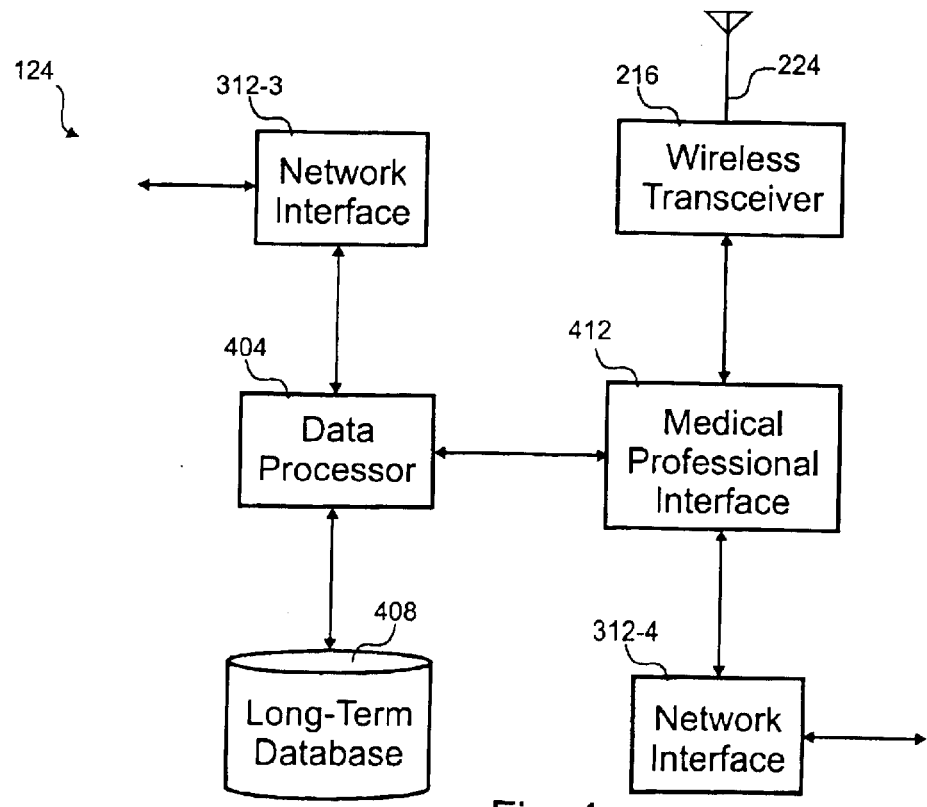
FIG. 4 is a block diagram of an embodiment of a monitoring center.

Referring next to FIG. 4, a block diagram of an embodiment of a monitoring center 124 is depicted. This embodiment uses the network interface 312-3 to communicate with the network interfaces 312-1, 312-2 of the aggregation nodes 112. A data processor 404 stores medical data for each patient 104 in a long-term database. Other information on the patient 104 is also stored in the long-term database 408. Data from sources other than the aggregation node 112 can be stored, such as circulating brain natriuretic peptide level test information for a patient 104.

Medical professionals 128 use a browser or other software interface to interact with the medical professional interface 412 through a wired or wireless connection. Web pages allow the medical professional 128 to ask questions or the patient or create questionnaires that are relayed to the aggregation node 112. The medical professional 128 can enter notes and other information into the long-term database 408 using the medical professional interface 412. Tools available through the medical professional interface 412 allow viewing the medical data using different diagrams and charts. To alert the medical professional 128 of potential problems discernable from the medical data, threshold events can be programmed into the data processor 404. The medical professional 128 can also indicate the action to be taken when a threshold event is satisfied. For example, a pager message could be sent to the medical professional 128 or a reminder message could be sent to the aggregation node 112 to remind the patient of something.

Figure 5A:
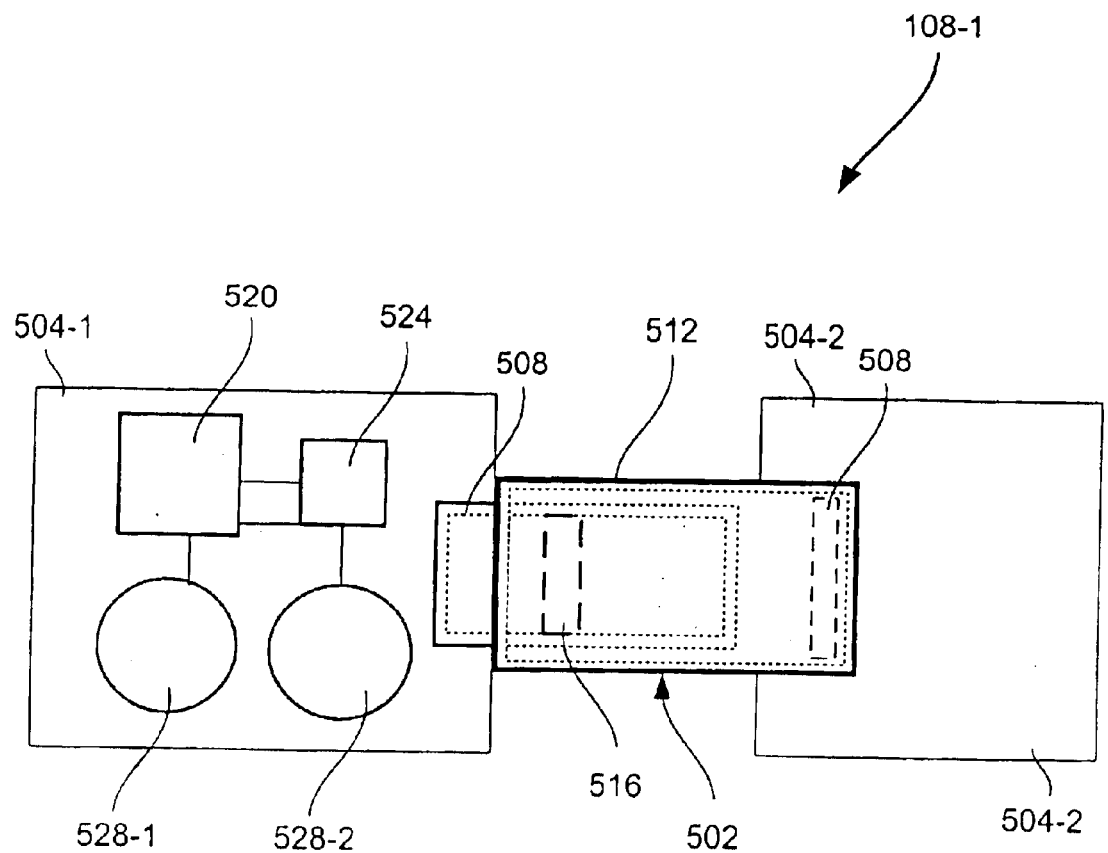
FIG. 5A is a top plan view of an embodiment of a data gathering device that ultrasonically measures respiration.

With reference to FIG. 5A, a top plan view of an embodiment of a data gathering device 108-1 is shown that ultrasonically measures respiration. This data gathering device 108-1 measures chest wall movement as a function of time using ultrasonic time-of-flight measurements. Included in the data gathering device 108-1 are one or more batteries 528, a sensor 502, adhesive pads 504, a first integrated circuit (IC) 524, and a second IC 520. The embodiment shown in FIG. 5A has the protective cover removed such that the internal components are visible. It is to be understood, that a water-resistant enclosure surrounds the sensor for protection while bathing and showering. Other embodiments could have a water penetrable enclosure and could be removed prior to exposure to water. The approximate area of the patient's skin covered by the sensor is two square inches.

This embodiment has two coin-shaped batteries to power the data gathering device 108-1. The batteries may or may not be end-user replaceable. Some embodiments may have rechargeable batteries. Because the power requirements are low, the device is expected to have a life of at least one year. In some circumstances, an embodiment may have no batteries at all and receive power with a wire from an aggregation node 112-2.

There are two adhesive pads 504 that couple the data gathering device 108-1 to the body of the patient 104. The adhesive pads are biocompatible with a patients skin. Some embodiments allow replacement of the adhesive pads 504, and other embodiments do not such that the sensor is for a single use. The adhesive pads 504 are shaped with a curve to conform with the shape of the chest wall.

The sensor 502 includes a low-power ultrasound transducer 516 that measures the distance between two points with a fluid path between those points. An inner cylinder 508 holds the transducer 516. The inner cylinder 508 is opened at the end enclosed by an outer cylinder 512. The transducer 516 produces a signal that is reflected off a closed end of the outer cylinder 512 and that signal is read once again. The transducer 516 is aligned in parallel and is coaxial with the closed end reflector.

The transducer 516 is ceramic and shaped like a disk, although other embodiments could use other materials and shapes. To act as a reflector, the closed end of the outer cylinder 512 is disk-shaped and made of stainless steel, but other shapes and materials could be used. The transducer 516 transmits a short signal that lasts less than a microsecond, for example. The short signal travels through the fluid path, is reflected by the reflector and then returns to the transducer 516 where it is detected and processed by the electronics. The time it takes for the signal to travel between the town points provides a means to calculate the distance between two points. This distance is given by the time-of-flight multiplied by the speed of sound in the coupling fluid divided by two. The short signal is repeated over time to determine a profile for the breathing patterns of the patient 104.

Figure 5B:
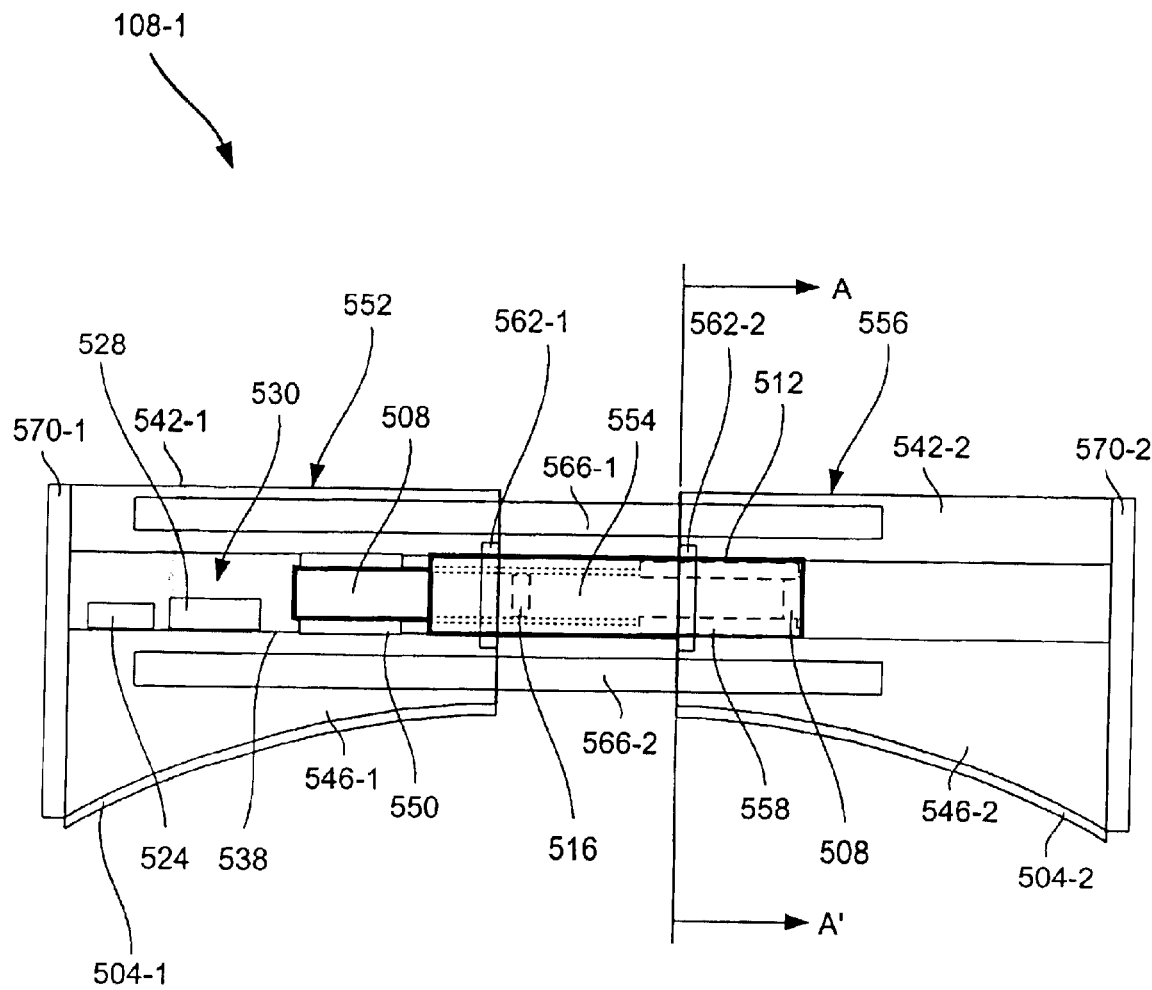
FIG. 5B is a right side elevation view of the embodiment of the data gathering device of FIG. 5A.
Figure 5C:
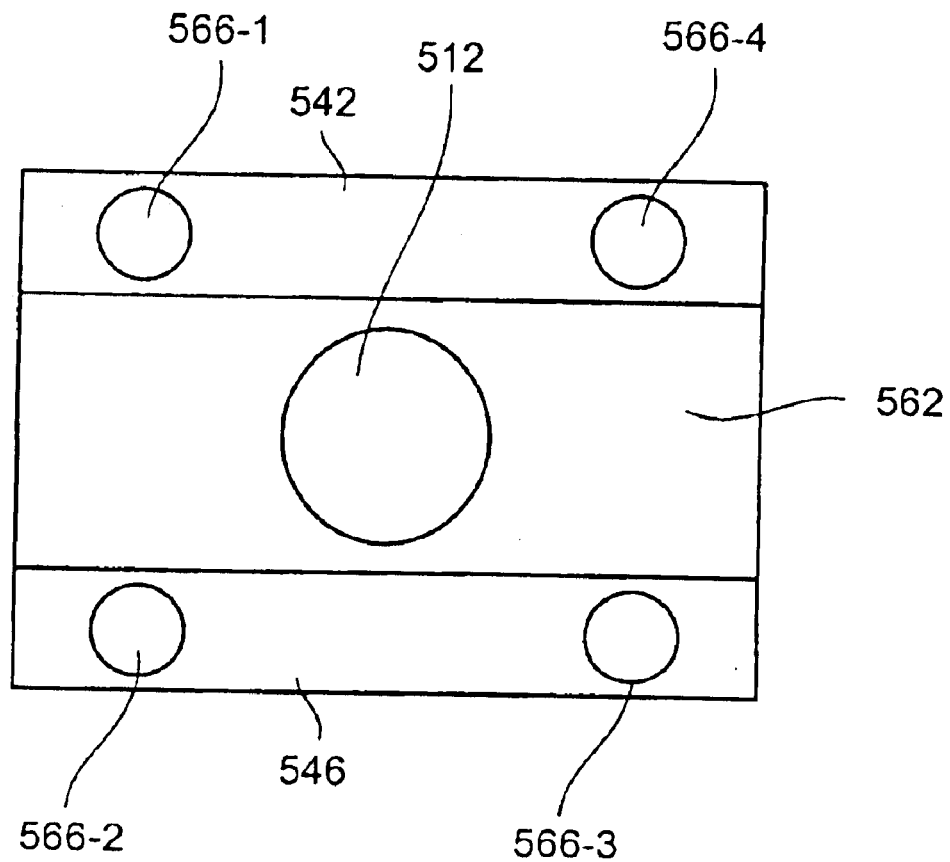
FIG. 5C is a sectional view of the embodiment of the data gathering device along the cross section defined by A–A' in FIG. 5B.

Referring to FIGS. 5B and 5C, a right-side elevation view of a cross-section of the embodiment of the data gathering device 108-1 of FIG. 5A is shown in FIG. 5B and a sectional view of the embodiment of the data gathering device 108-1 along the cross section defined by A–A' in FIG. 5B is shown in FIG. 5C. The inside cylinder 508 is half-filled with fluid. A disc-shaped piezoelectric ceramic transducer 516 forms one end of a fluid-filled chamber 554. The transducer 516 is connected to the electronics of the data gathering device 108-1 through two wire electrodes (not shown) that are 40 AWG or smaller in this embodiment. The other end of the fluid-filled chamber 554 is attached to the outside cylinder 512 through miniature bellows that allow the two cylinders 508, 512 to move with respect to each other with minimal friction. A lubricant is used between the two cylinders 508, 512 to reduce sliding friction. The diameter of the outside cylinder 512 is only slightly larger than the diameter of the inside cylinder 508. The type of fluid used in the inside cylinder for this embodiment is a non-ionic fluid such as glycol or any similar formulation. The inside cylinder 508 includes a stainless steel disc reflector 508 positioned at the far end of the fluid-filled chamber 554.

The inside cylinder 508 is attached to a left side 552 of the data gathering device 108-1 with a fastener 550 or permanent adhesive. The outside cylinder is similarly attached to a right side 556 of the data gathering device 108-1. Four aligning rods 566 are employed to keep the left and right sides 552, 556 aligned during operation. Stainless steel or another rigid material could be used for the aligning rods 566. The aligning rods 566 are rigidly attached to the left side 552 by being embedded into the left top plate 542-1 and are free to slide in out of the right top plate 542-2 of the right side 556. A lubricant is used to reduce sliding friction between the rods 566 and metal plates 542. Alternatively, the aligning rods 566 may incorporate linear bearings to reduce friction.

Each side 552, 556 has four metal plates 542, 546, 562, 570 that act as enclosures to provide protection for the electronic and mechanical parts of the data capture device 108-1 as well as maintain parallelism and alignment between transducer 516 and reflector 508. Each of the left and right sides 552, 556 includes a middle plate 562, a top plate 542, a bottom plate 546, and an end plate 570. To complete the device assembly, the right and left middle plates 562 include an opening to allow insertion of the cylinders 508, 512 for each side 552, 556. FIG. 5C shows a cross section of the data capture device 108-1 at a plane defined by the right metal plate 562-2.

The plates 542, 546, 562, 570 that make up the enclosure can be made from a light metal such as aluminum, aluminum alloy, titanium, titanium alloy, or other light metals. Further, the plates 542, 546, 562, 570 can be made from a high impact engineering plastic or plastic composite such as carbon fiber reinforced plastic.

The bottom metal plate 546 on each side 552, 556 has a curved surface compatible with the curvature of the patient 104 in the chest area. Since variations exist in human measurements, a number of different curvatures may be available to the patient 104. The bottom of the curvature will allow the incorporation of a detachable two-sided adhesive pad 504 that enables the patient 104 to attach the pad 504 to the device 108 as well as herself. A thin layer of padding between two layers of adhesive will further facilitate attachment to varying chest topologies.

The electronic components of the data gathering device 108 are housed inside an electronics cavity 530. The components are surface mounted on a flex circuit 538 that includes the circuit traces to connect the electronic components. This embodiment includes electronic components such as two ICs 520, 524, one or two miniature batteries 528 and the sensor 502.

The first IC 524 is an analog device which incorporates a transmit circuit, a receive circuit and a receive pulse amplifier. The first IC 524 is powered from a low voltage source, for example, in the 1 to 2 V range. The first IC 524 receives signals from the second IC 520 to turn on, transmit pulses to the ultrasound transducer 516, receive return pulses off the reflector 508, amplify the return pulses and return them to the second ID 520. In this embodiment, the first IC 524 operates in the frequency range of between 5 and 20 MHz. The transmit pulse is between 0.5 and 10 Volts peak-to-peak and is a one to two cycle square wave or sinusoidal wave.

The pulses are applied to the ultrasonic transducer 516 and they are converted into ultrasonic waves. The ultrasonic waves travel through fluid-filled chamber 554, are reflected off the stainless steel plate 508 at the far end and travel back to the transducer 516 for conversion back into electrical pulses. The received pulses are amplified by about 15 to 30 db before being passed to the second IC 520.

The second IC 520 converts the received pulses to digital, digital stores the medical data, performs logic control, a tracks time with a clock, transceives medical data, and includes an RF transmit/receive antenna. In this embodiment, when the signals are received from first IC 524 they are digitized, the distance for each event is calculated and the data is stored until a monitoring cycle (one to five minutes) is complete. When data for a complete cycle is accumulated then the RF antenna transmits those data wirelessly to the aggregation node for further processing.

The RF antenna in the second IC 520 transmits and receives signals wirelessly up to 30 ft from the sensor at a frequency of 2.4 GHz and at the rate of 771 kbits/s, even though other frequencies and rates may be used. Some embodiments could have longer ranges, such as 300 ft. with other bitrates.

The data gathering device 108 gathers medical data in regular intervals, with the preferred interval being hourly, even though other regular intervals may be chosen. Some embodiments could gather medical data continually, for example, when monitoring respiration for sudden infant death syndrome. The data gathering device 108 is controlled by a timing device incorporated into the second IC 520 that regulates its powering-up, the collection and transmission of data as well as the "down" cycle implementation where the data gathering device 108 is in a sleep mode. At the same time, the data gathering device 108 can be made to initiate an acquisition cycle through an external command transmitted by the aggregation node 112 to the RF antenna of second IC 520. It is understood that these commands can also be relayed to the data gathering device 108 from the monitoring center 124.

Figure 6:
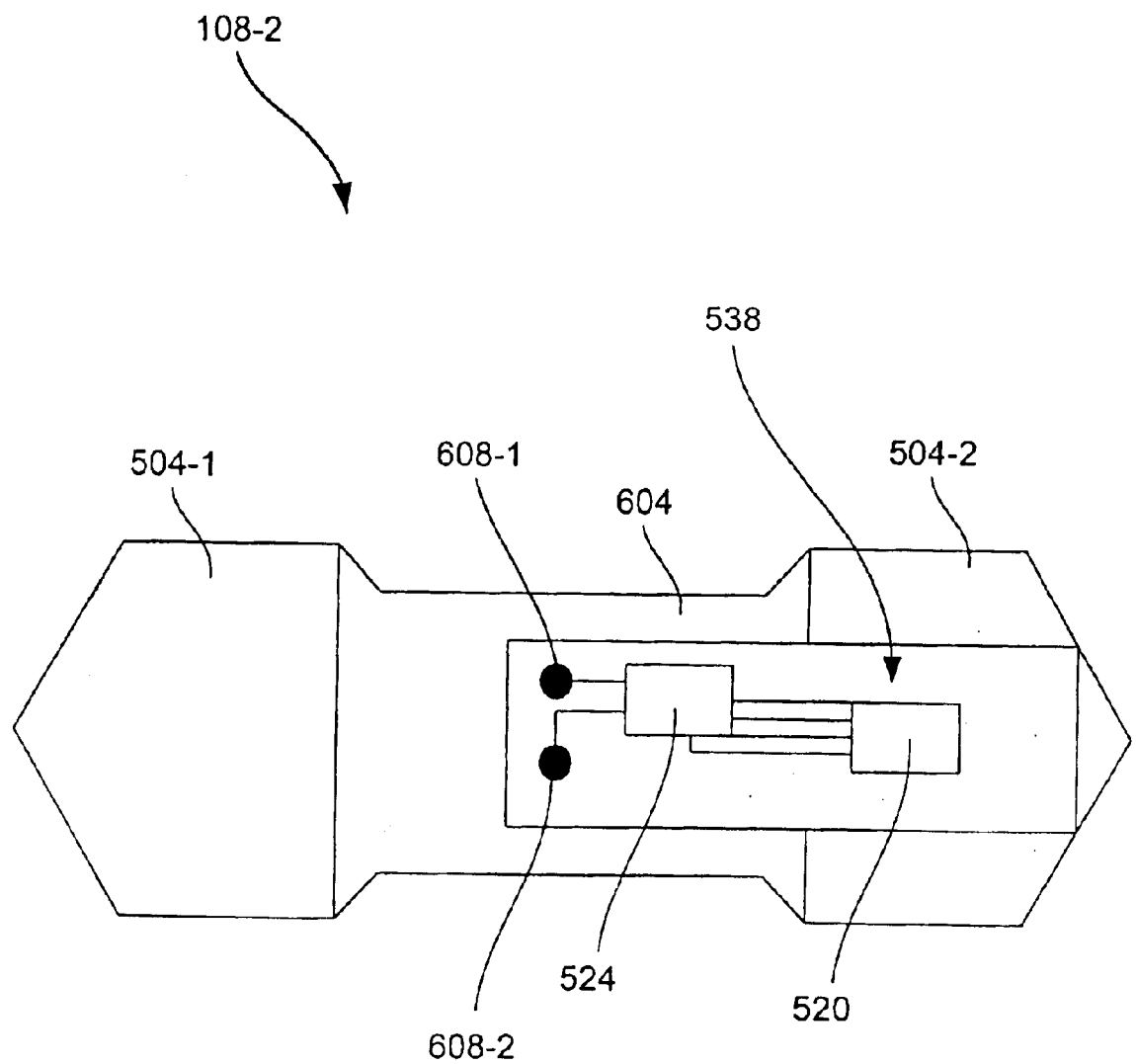
FIG. 6 is a top plan view of an embodiment of a data gathering device that piezoelectrically measures respiration.

Referring to FIG. 6, a top plan view of an embodiment of a data gathering device 108-2 is shown that piezoelectrically measures respiration. A piezoelectric sensor 604 made of PVDF is used to monitor chest wall motion. PVDF develops surface charge/voltage both in the 33 and 31 crystallographic direction when stretched. Two electrodes 608 mounted to the piezoelectric sensor 604 sense the surface charge. Processing of the surface charge value produces chest wall movement measurements. By implication, the respiration is determined from the chest wall movement information.

Figure 7:
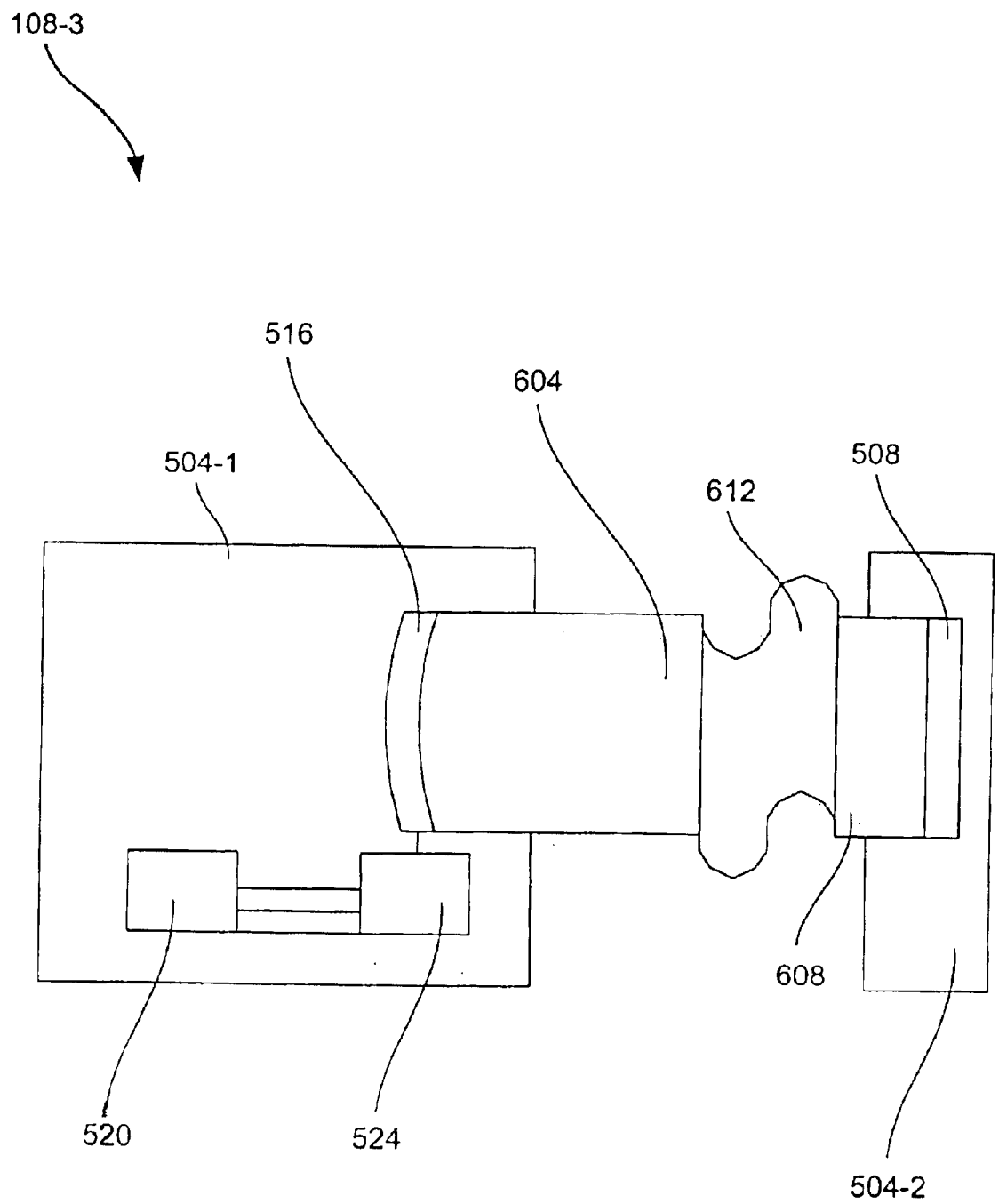
FIG. 7 is a top plan view of another embodiment of a data gathering device that ultrasonically measures respiration.

With reference to FIG. 7, a top plan view of another embodiment of a data gathering device 108-3 is shown that ultrasonically measures respiration. A transducer portion 604, a compressible portion 612 and a reflector portion 608 make up a fluid chamber that allows the ultrasonic measurement. As the chest wall expands and contracts, so does the compressible portion 612.

Figure 8:
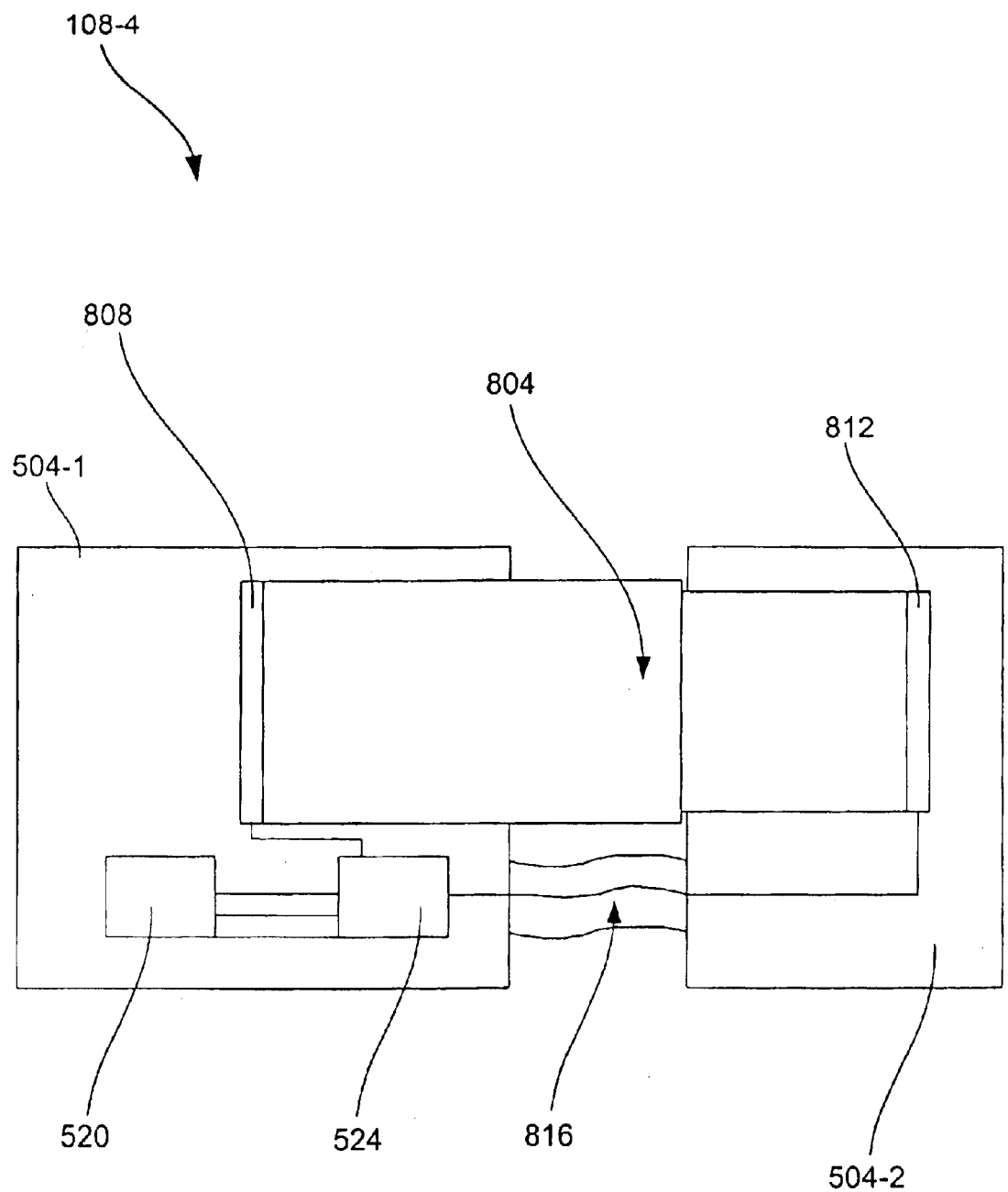
FIG. 8 is a top plan view of an embodiment of a data gathering device that capacitively measures respiration.

Referring to FIG. 8, a top plan view of an embodiment of a data gathering device 108-4 is shown that capacitively measures respiration. The sensor 804 includes two capacitive cylinders 808, 812. As the chest wall expands the capacitive coupling is weaker between the capacitive cylinders 808, 812. The changes in capacitance are translated into chest wall motion. A flexible cable 816 connects the first IC 524 to the right capacitive cylinder 812.

Figure 9:
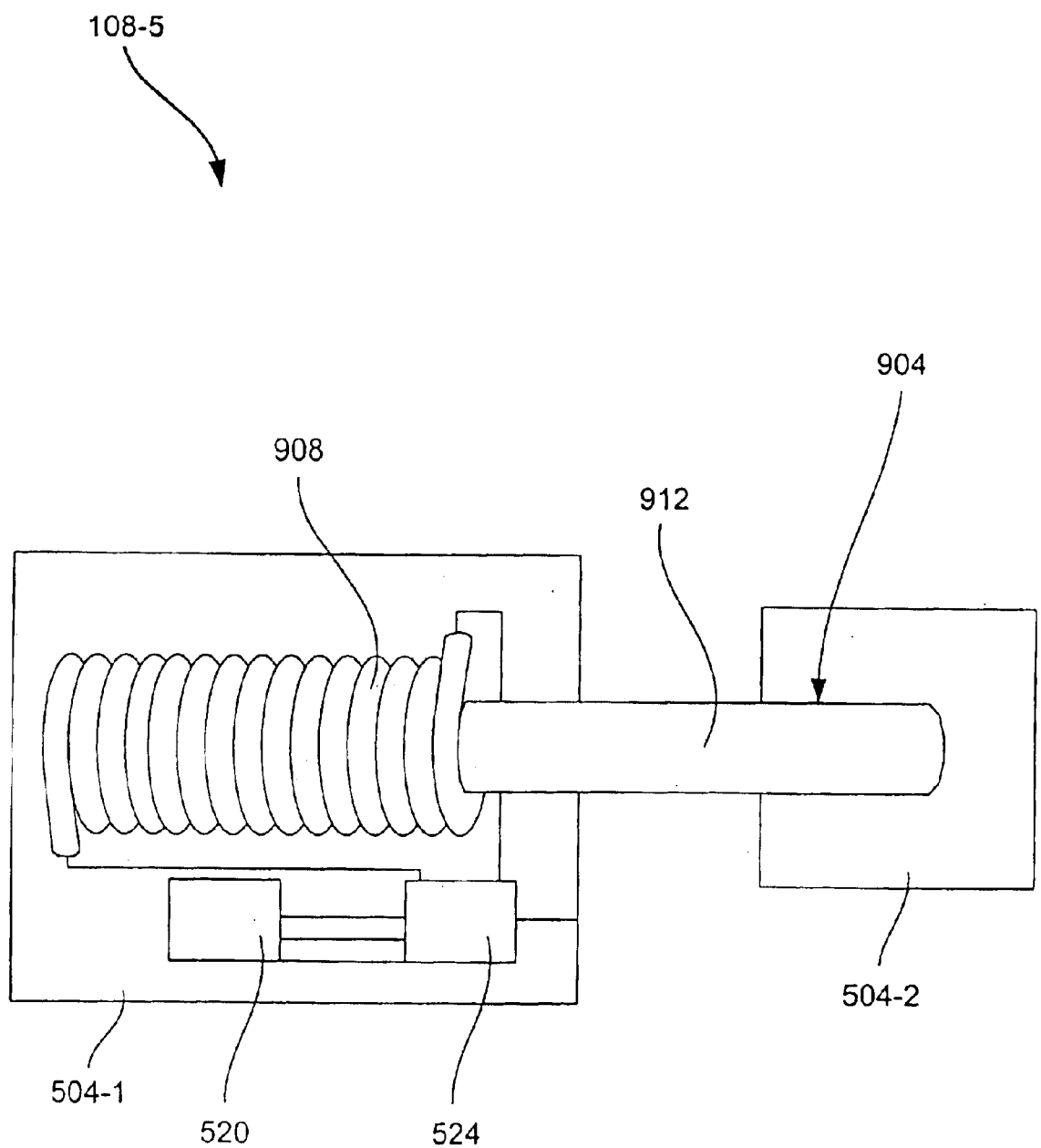
FIG. 9 is a top plan view of an embodiment of a data gathering device that inductively measures respiration.

With reference to FIG. 9, a top plan view of an embodiment of a data gathering device 108-5 is shown that inductively measures respiration. A linear displacement sensor 904 measures changes in inductance as a pin 912 is inserted into a coil 908. Variations in inductance is correlated to chest wall movement.

Figure 10A:
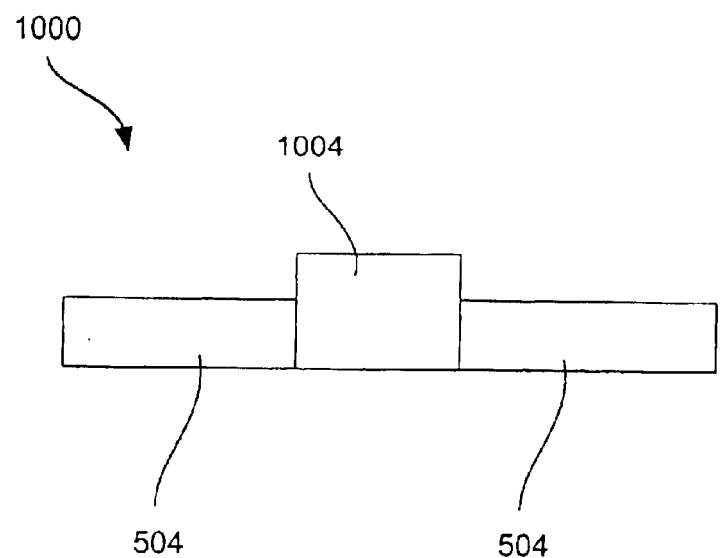
FIG. 10A is a side sectional view of an embodiment of a blood flow sensor.
Figure 10B:
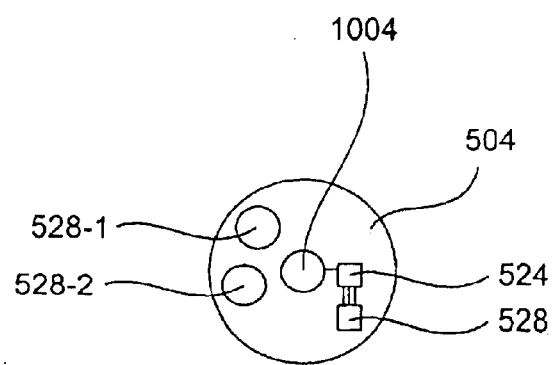
FIG. 10B is a top plan view of the embodiment of the blood flow sensor of FIG. 10A.

Referring to FIGS. 10A and 10B, two views of an embodiment of a blood flow sensor 1000 are shown. A Doppler ultrasound sensor 1004 suitable for blood flow speed measurement in the ascending aorta or other artery is used. The sensor 1004 transmits pulsed wave ultrasound from Doppler transducer attached to the suprasternal area into the ascending aorta. Blood flow is measured as function of time. Some embodiments could use this ultrasound sensor 1004 to measure cardiac output, for example.

Figure 11:
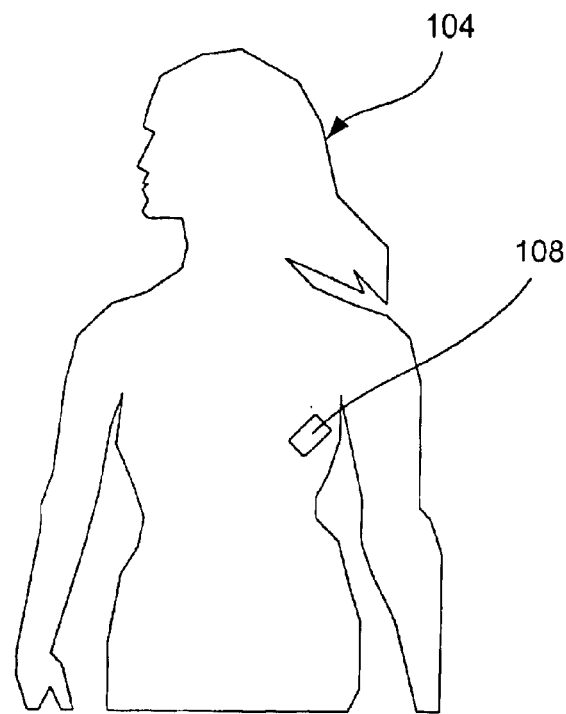
FIG. 11 is a depiction of an embodiment of the data gathering device attached to the patient.
Figure 12:
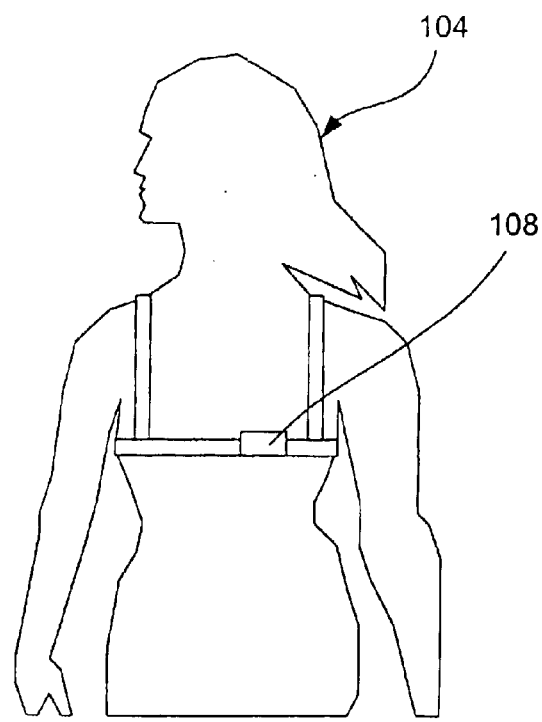
FIG. 12 is a depiction of another embodiment of the data gathering device attached to the patient.

With reference to FIG. 11, a depiction of an embodiment of the data gathering device 108 attached to the patient 104 is shown. The data gathering device 108 is attached near the chest area to measure movement of the chest wall during breathing. Other chest or abdominal areas are also suitable locations for device attachment. The adhesive pads are detachable and replaceable during repeated use. An alternative approach to the attachment of the device is the use of straps as shown in the embodiment of FIG. 12. The data gathering device 108 is inserted in a strap placed around the torso and supported by shoulder straps. When used in this fashion, no adhesive is used.

Figure 13:
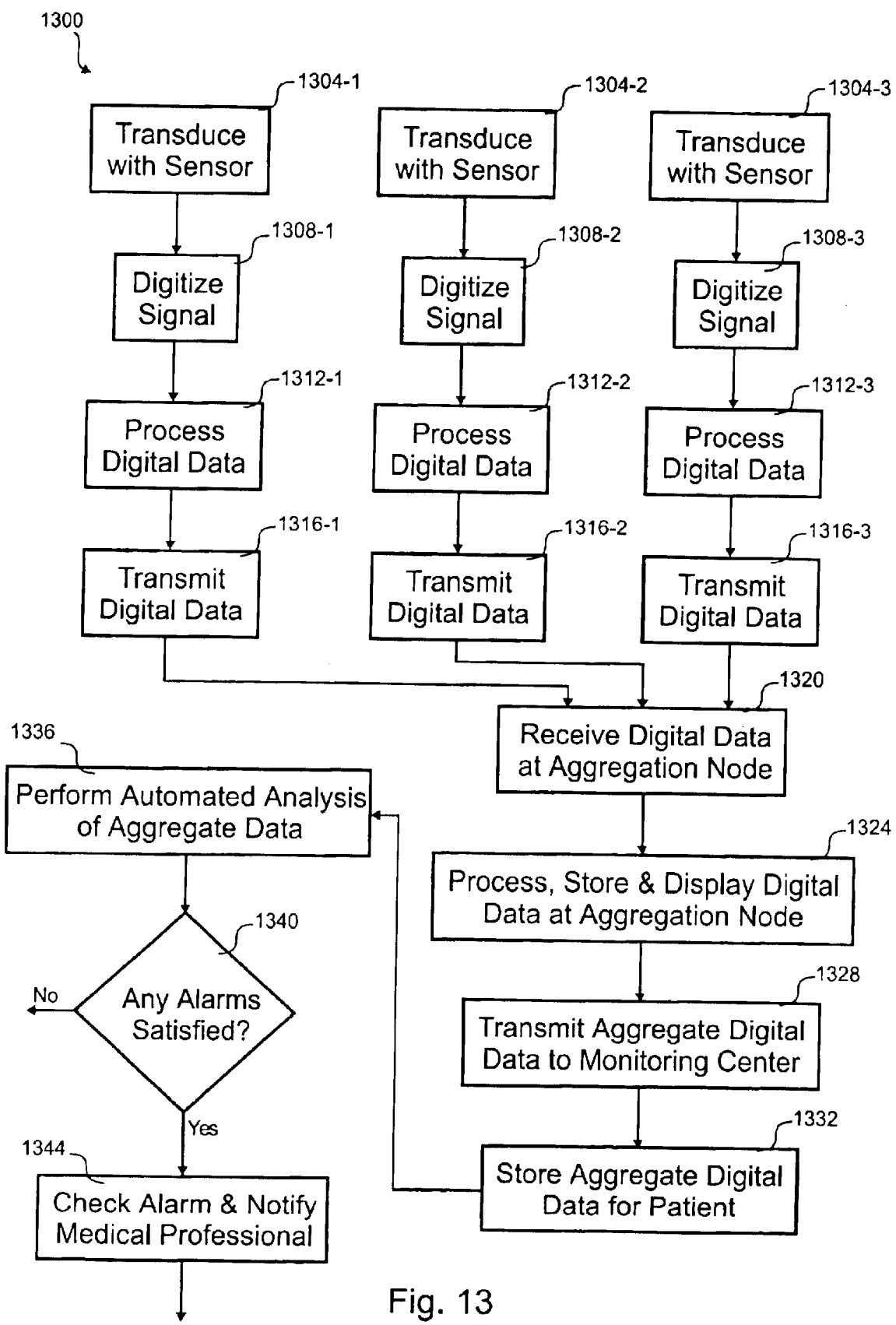
FIG. 13 is a flow diagram of an embodiment of a process for gathering cardiopulmonary data from the patient.

With reference to FIG. 13, a flow diagram of an embodiment of a process 1300 for gathering cardiopulmonary data from the patient is shown. This embodiment uses three data gathering devices 108, but other embodiments could use other amounts of data gathering devices 108. The depicted portion of the process 1300 begins in step 1304 where the sensor transduces a signal indicative of the parameter being measured. In steps 1308 and 1312, the signal is digitized and processed. The processing may include any number of calculations. Further, the measurements may be taken intermittently in some embodiments to reduce power consumption. In step 1316, the processed digital data is transmitted to the aggregation node 112. Encryption and/or compression can be used for the wireless link between the data gathering device 108 and the aggregation node 112.

In step 1320, the aggregation node 112 receives digital medical data from the data gathering devices 108. The digital medical data is further processed, stored and may be displayed at the aggregation node 112 in step 1324. In some circumstances, the medical data is displayed, but the patient 104 may have control over the display ability. The medical professional 128 can design how the medical data is displayed on the aggregation node.

In a single data stream, the digital medical data is transmitted from the aggregation node 112 to the monitoring center in step 1328. The monitoring center 124 receives the digital medical data from all the aggregation nodes 112 in the system 100. Some embodiments may transmit the information directly to a computer system of the medical professional 128 such that the computer system fulfills the role of the monitoring center 124 for the patients 104 of the medical professional 128.

In step 1332, the monitoring center 124 stores the received digital medical data in the long-term database 408. Any further processing and automated analysis is performed on the aggregate medical data received from each aggregation node 112 in step 1336. Test are performed to see if any defined thresholds are satisfied such that any alarms are activated as determined in step 1340. The alarm conditions are acted upon in step 1344. One possible action is to notify the appropriate medical professional 128. Other alarms, for example, could result in questions being sent to the aggregation node 112 for the patient 104.

Figure 14:
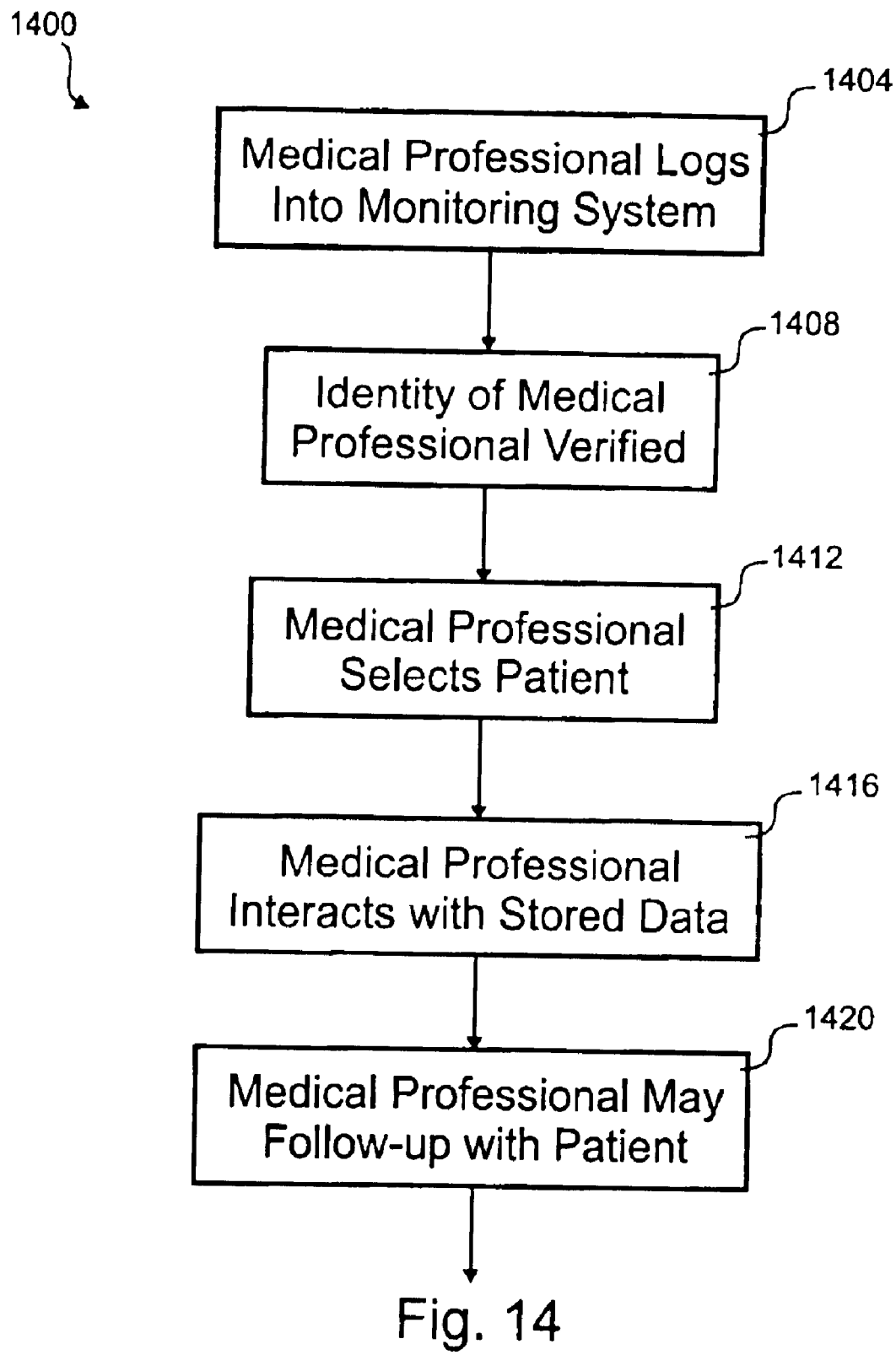
FIG. 14 is a flow diagram of an embodiment of a process for a medical professional to interact with the monitoring center.

Referring to FIG. 14, a flow diagram of an embodiment of a process 1400 for a medical professional 128 to interact with the monitoring center 124 is shown. The medical professional 128 uses the monitoring center 124 as an application service provider (ASP) that maintains information on patients 104. The portion of the process 1400 depicted begins in step 1404 where the medical professional logs onto the monitoring system 124 using a web browser. Some embodiments, could use application software other than a browser for this interaction.

In step 1408, the identity of the medical professional is verified using a user identifier and password or other method for verification. The medical professional 128 indicates which patient 104 to display information on in step 1412. The medical professional 128 interacts with the information stored in the long-term database 408 in step 1416. For example, ischemia risk stratification could be determined from this interaction. Different graphs and treatment scenarios are formulated by the monitoring center 124 to aid the medical professional 128. Some embodiments, could e-mail this information on patients 104 to the medical professional 128 a predefined intervals. In step 1420, the medical professional 128 may follow-up with a questionnaire or message to the patient 104. Further the medical professional may design new threshold conditions and alarms or may interact with the patient on the phone or in person.

Some embodiments could do trend analysis of the information in the long-term database 408 to predict progression of disease. The medical data for the patient 104 could be compared against models derived from historical profiles to predict how the disease may progress. Different therapies can be hypothetically applied to the patient data and the likely response to those therapies could be displayed for the medical professional 128.

Figure 15:
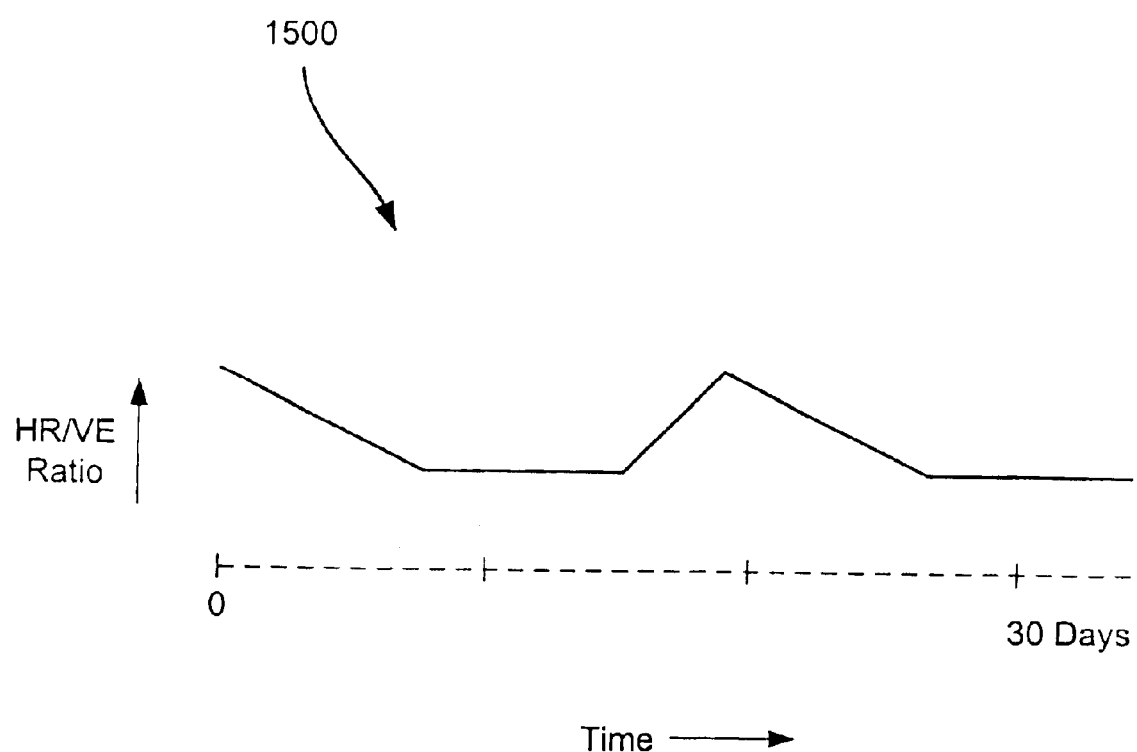
FIG. 15 is a chart of an embodiment of heart rate to ventilation ratio as it varies for a patient over time.

With reference to FIG. 15, a chart of an embodiment of heart rate to ventilation ratio as it varies for a patient over time is shown. This is but one example of the types of diagnostic charts that are made available by the monitoring center 124 to the medical professional 128. The ratio divergence from the center or baseline of the chart may indicate a worsening condition or decompensation status, whereas a convergence of the trend plot towards the center line of the chart may indicate an improvement in the CHF patient's condition. A flat-level line would indicate patient 104 stability. In some embodiments, such a trend could be provided as a single or multiparameter graphic with standard deviation and normal range indicators.

Following are brief descriptions of how the measurement of heart rate (HR) and ventilation (VE) with the invention can enhance the prognostic monitoring of congestive heart failure (CHF) patients and other cardiovascular disease patients. New terms are introduced for data presentation and analysis that describe how the CHF patient parameters can be derived from "gold standard" methods in order to provide accurate function of the proposed sensors for HR, VE and blood pressure.

Inference Templating (IT) is a term which has been selected for description of how known "gold standard" parameters can be derived via a proven, known high correlation of the "new" parameter to the "gold standard" one. In this way, monitoring the "new" parameter provides the "gold standard" parameter by an inferential relationship. An example of IT is with the correlation of the VE to the volume of $CO_2$ expired ($VCO_2$) slope, a proven independent, powerful predictor of CHF patient risk or mortality to the tidal volume (VT) changes during a known amount of exercise performed by the CHF patient such as a flight of stairs with a fixed distance and fixed percentage incline. Since the correlation between VT and the VE to $VCO_2$ slope is high, the VT parameter and its changes during exercise can be used as a substitute or "inference template" for the "gold standard" parameter of VE to $VCO_2$ slope. As a "back-up" or replacement technology to determine the VE to $VCO_2$ relationship during rest or exercise in CHF or heart disease patients, a miniature, comfortable, light weight mouthpiece can be used to measure expired $CO_2$ tension or "concentration" which then would provide an indirect correlate to the "gold standard" of measured $CO_2$ volumes, using an IT algorithm, as described below.

Another example of IT is how the VE changes during linear, incremental, exercise in healthy or heart disease patients. The correlation is represented by a "curvilinear" function. VT also displays the same type of "curvilinear" relationship during incremental exercise. Since VT is known to correlate highly with VE, it is proposed that VT, as sensed by the herein the described sensor technologies, serve as the dominant, single sensor to "drive" a device such as an intracardiac pacemaker for restored rate response or HR reserve in an individual with the need for rate adaptive pacing without the need to measure the respiratory rate. We note that CHF patients display chronotropic incompetence during mild to moderate exercise due to their high sympathetic drive or autonomic imbalance. The VT sensor may also be used in patients with CHF who require or may benefit from bi-ventricular pacing. The VT sensor, either "external" from the pacemaker/defibrillator or incorporated in its internal circuitry could be used to adjust right ventricle (RV) to left ventricle (LV) synchronization intervals, atrial ventricular (AV) intervals or even the rate response curve profile when VT changes or reflects alterations in lung function due to changes in cardiac filling pressures and ventilation to perfusion matching.

Yet another example of IT is the correlation of increased VE to heart rate variability (HRV) in CHF patients. Since the correlation is high between VE and HRV, inferences can be made concerning the HRV estimates or changes in the CHF patient, aside from or supportive of. Aside from or supportive of actual calculation HRV via actual "Holter" HR monitoring. IT is not limited to the above mentioned physiologic parameters, but can be applied to other sensors for monitoring, acute or chronic, valuable, clinically prognostic data in patients with metabolic, pulmonary, or cardiovascular diseases.

In terms of new parameters which can be derived from the herein proposed sensors for HR and VE (VT), a "rolling" VE or VT dispersion or tidal volume variability (VTV) or ventillation variability (VEV) parameter can be calculated, similar to the way HRV is determined.

In addition, the VT or VE sensor can be used to analyze the chronic or acute or occurrence of periodic breathing, a known phenomena in CHF patients with "spin-off" applications for monitoring of changes in apnea in infants or drug-induced changes in lung function in patients on anti-arrhythmic medications such as amiodarone or in CHF patients on medications known in some cases to adversely effect lung function. In addition, another application of the Doppler ultrasound sensor described in relation to FIGS. 10A and 10B above will is a peripheral ankle-strapped device to assess tissue thickness changes as a result of edema in the CHF patient. The device will essentially emit ultrasound waves from the skin's epidermal layer to a distal portion of the tibia, fibula, both, or some other bone and calculate the reflection transit time as a correlate to tissue thickness. Such a device will also be used to provide confirmation analysis of body weight changes as a result of fluid retention in the CHF patient.

The methods and algorithms for the wireless transmission of key physiologic data, acute and chronic trending displays of data are provided to the physician by software which utilizes Frequent Point Analysis (FPA) or Frequent Point Plotting (FPP) techniques with "zoom-in" functions and filters. Such data displays will essentially eliminate "gap" clinical information which currently exists with technology based within the hospital, clinic, or even at the patient's home with intermittently scheduled visits. Trending display can provide single parameter trending graphics analysis or multiparameter displays based upon indexing of two or more parameters together to enhance the "power" of the trend. Kaplain Meyer Plots will also be ongoing to provide the physician on actual patient risk or mortality profiles. Multicongruent Data Trending (MDT) with graphic comparisons will enhance the physician's rapid recognition of the patient's stability, improvement, or deterioration status. The physiologic parameters to be included in the above stated graphics techniques will include ventilation (VT or VE), heart rate, peripheral tissue edema, blood pressure and pulse pressure, HRV, VEV, VTV, rate pressure product, the VT to $VCO_2$ correlate, HRV to VT ratio, and VT or HR to VE ratio, but not be limited to the above. For example, trending analysis could be incorporated for circulating brain natriuretic peptide levels (BNP) which is an indicator of the severity of and patient risk from CHF. Automatic Trend Scanning (ATS) may be used to alert the physician to potentially critical data points for immediate patient contact, scheduled clinic visit and altered therapy.

While the principles of the invention have been described above in connection with specific apparatuses and methods, it is to be clearly understood that this description is made only by way of example and not as limitation on the scope of the invention.

What is claimed is:

1. A system for monitoring health information of a plurality of patients, the system comprising:
   a data gathering device comprising:
      a respiration sensor,
      a wireless transmitter, and
      a self-contained power source;
   a node wirelessly coupled to the data gathering device;
   a wide area network coupled to the node; and
   a monitoring center located remote to the node and coupled to the wide area network, wherein:
      the respiration sensor measures movement between two points on skin of a one of the plurality of patients where the two points are proximate to the one's chest,
      the two points are between the respiration sensor and the skin of the one, and
      an area of two square inches or less is covered by the data gathering device.

2. The system for monitoring health information of the plurality of patients as recited in claim 1, further comprising a plurality of nodes where each is linked to both a different patient and the wide area network.

3. The system for monitoring health information of the plurality of patients as recited in claim 1, wherein the monitoring center reports medical data relating to diagnosing at least one of: lung disease, heart disease, sleep apnea, arrhythmia, ischemia, congestive heart failure, and sudden infant death syndrome.

4. The system for monitoring health information of the plurality of patients as recited in claim 1, wherein the data gathering device further includes a digitizer to digitize an analog signal from the respiration sensor.

5. The system for monitoring health information of the plurality of patients as recited in claim 1, wherein the node comprises:
   a portable device worn on one of the plurality of patients, and
   a wireless connection to the wide area network.

6. The system for monitoring health information of the plurality of patients as recited in claim 1, wherein the wide area network includes at least one of: a wireless datalink, a telephone line, an Internet connection, and a private network.

7. The system for monitoring health information of the plurality of patients as recited in claim 1, wherein the wireless transmitter has a range of up to about 300 feet.

8. The system for monitoring health information of the plurality of patients as recited in claim 1, further comprising a second data gathering device comprising at least three of the following:
   a heart rate sensor,
   a pulse pressure sensor,
   a blood pressure sensor,
   an oxymetry sensor,
   an exhaled CO2 sensor,
   an electrocardiogram sensor,
   a peripheral tissue edema sensor,
   a second wireless transmitter, and
   a second self-contained power source.

9. The system for monitoring health information of the plurality of patients as recited in claim 1, further comprising a medical professional interface proximate to the monitoring center, wherein the medical professional interface provides heart rate and respiration data to a medical professional.

10. The system for monitoring health information of the plurality of patients as recited in claim 1, wherein:
    the data gathering device produces a digital signal representative of an analog signal from the sensor, and
    the data gathering device processes the digital signal with the data gathering device.

11. The system for monitoring health information of the plurality of patients as recited in claim 1, wherein the monitoring center is provided with heart rate and ventilation data for the one.

12. The system for monitoring health information of the plurality of patients as recited in claim 1, wherein ventilation is determined by the respiration sensor measuring movement of the two points over time.

13. A method for remotely monitoring heart rate and ventilation of a patient, the method comprising:
    measuring at least two of heart rate, chest wall movement, blood pressure, blood oxygen levels, exhaled CO2 levels, and peripheral tissue edema with a data gathering device;

producing digital medical data indicative of the measuring step;

wirelessly transmitting the digital medical data to a node;

transmitting the digital medical data over a wide area network from the node to a remote location;

receiving circulating brain natriuretic peptide level data for the patient;

analyzing the circulating brain natriuretic peptide level data; and processing the digital medical data at the remote location to produce heart rate and ventilation data for the patient.

14. The method for remotely monitoring heart and/or lung function of the patient as recited in claim 13, further comprising steps of:

measuring one more of heart rate, chest wall movement, blood pressure, blood oxygen levels, exhaled CO2 levels, and peripheral tissue edema with a second data gathering device;

producing second digital medical data related to the immediately-preceding measuring step;

wirelessly transmitting the second digital medical data to the node;

transmitting the second digital medical data over the wide area network to the remote location; and processing the second digital medical data at the remote location.

15. The method for remotely monitoring heart and/or, lung function of the patient as recited in claim 14, further comprising a step of displaying information related to the first and second digital medical data for a medical professional.

16. The method for remotely monitoring heart and/or lung function of the patient as recited in claim 13, wherein the node comprises:

a portable device worn on the patient, and a wireless connection to the wide area network.

17. The method for remotely monitoring heart and/or lung function of the patient as recited in claim 13, wherein the measuring step comprises measuring with at least one of:

a heart rate sensor, a respiration sensor, a pulse pressure sensor, a blood pressure sensor, an oxymetry sensor, an exhaled CO2 sensor, an electrocardiogram sensor, and a peripheral tissue edema sensor.

18. The method for remotely monitoring heart and/or lung function of the patient as recited in claim 13, further comprising a step of providing information related to the digital medical data at the node in a form recognizable by a human.

* * * * *